United States Patent [19]

Chao

[11] Patent Number: 4,861,504
[45] Date of Patent: Aug. 29, 1989

[54] OIL ADDITIVE HAVING REDUCED LACQUER FORMING TENDENCIES

[75] Inventor: Tai S. Chao, Olympis Fields, Ill.

[73] Assignee: Atlantic Richfield Company, Los Angeles, Calif.

[21] Appl. No.: 148,278

[22] Filed: Jan. 25, 1988

[51] Int. Cl.$^4$ ................ C01M 105/08; C01M 105/72
[52] U.S. Cl. ........................................ 252/48.2; 252/45
[58] Field of Search ................ 252/427, 48.2, 45, 48.6

[56] References Cited

U.S. PATENT DOCUMENTS

| | | | |
|---|---|---|---|
| 2,459,114 | 1/1949 | Oberright | 252/42.7 |
| 2,766,852 | 8/1956 | Stevens | 44/78 |
| 2,862,883 | 12/1958 | Hughes | 252/33.4 |
| 3,014,868 | 12/1961 | Munns | 252/39 |
| 3,036,003 | 5/1962 | Arthur | 252/51.5 R |
| 3,340,190 | 9/1967 | Deluga | 252/42.7 |
| 3,368,972 | 2/1968 | Otto | 252/47.5 |
| 3,429,812 | 7/1969 | Kivelevich | 252/42.7 |
| 3,883,501 | 5/1975 | Malec | 252/48.2 |
| 3,912,707 | 10/1975 | Abbott | 252/42.7 |
| 3,992,308 | 11/1976 | Malec | 252/48.2 |
| 4,100,081 | 7/1978 | Dreher | 252/25 |
| 4,664,822 | 5/1987 | Hunt | 252/49.6 |

*Primary Examiner*—William R. Dixon, Jr.
*Assistant Examiner*—James M. Hunter, Jr.
*Attorney, Agent, or Firm*—James C. Fails; Arthur F. Zobal; Geofrey A. Mantooth

[57] ABSTRACT

An oil additive, particularly useful for railroad engines having reduced lacquer forming tendencies characterized by a novel alkaline earth phenate in which the normal tendency to form lacquers is reduced by the substitution of electron-donating groups; such as sulfur or tertiary amines for the secondary amine in the structural formula.

3 Claims, No Drawings

4,861,504

OIL ADDITIVE HAVING REDUCED LACQUER FORMING TENDENCIES

FIELD OF THE INVENTION

This invention relates to novel alkaline earth metal phenates that are oil soluble and employed in a lubricant to give improved oxidation resistance, detergency, antiwear characteristics and basicity. The improved phenates of this invention have reduced tendency to form lacquer and varnish deposits in the engine in which lubricants containing these additives are employed.

DESCRIPTION OF THE PRIOR ART

The prior art is replete with a wide variety of approaches to improve the oxidation and corrosion resistance, detergency, dispersancy, lubricity, basicity and other properties of engine oils and other lubricants. One type of additive which has been widely used to improve these properties for diesel engine oils, especially for railroad diesel engine oils, are the alkaline earth metal phenates.

There are three general types of alkaline earth phenates which are known in the prior art and used commercially in railroad and other diesel engine oils. They are differentiated by the bridging atoms between the aromatic nuclei of the phenols.

The first type is the sulfur-bridged phenates. They have one or more sulfur atoms between the aromatic nuclei and are prepared by treating alkylphenols with suitable sulfur compound, followed by treating with alkaline earth metal hydroxide. Examples of prior art patents using this approach include the follows:

U.S. Pat. Nos. 2,398,253, 2,406,041, 2,425,824, 2,449,026, 2,785,131, 3,320,163, 3,336,224, 3,367,867, Re. 29661.

British Pat. Nos. 1,094,609, 1,121,437, 1,164,417, 1,153,269.

The second type is the so-called carbon-bridged, or methylene-bridged, phenates. They have a $CH_2$ group between the aromatic nuclei and are prepared by treating alkylphenols with formaldehyde and alkaline earth metal hydroxide. Examples of prior art patents include:

U.S. Pat. Nos. 2,361,804, 2,375,222, 2,410,652, 2,453,850, 2,632,696, 2,736,701, 2,760,852, 2,833,719, 2,862,883, 2,913,412, 3,014,868.

The third type is the so-called nitrogen-bridged, or Mannich base type, phenates. They have $CH_2NHCH_2CH_2$ or other alkylene amine groups between the aromatic nuclei and are prepared by treating alkylphenols with formaldehyde and an alkylene polyamine, followd by treating with an alkaline earth metal hydroxide. Examples of prior art patents employing this approach include the follows:

U.S. Pat. Nos. 3,036,003, 3,057,800, 3,340,190, 3,368,972, 3,429,812.

Of the three types of alkaline earth phenates listed hereinbefore, the Mannich base type phenates are the most effective in providing oxidation and corrosion resistance to the engine oil. For this reason, the following abstracts are given of the patents cited in that section:

U.S. Pat. No. 3,036,003 describes a lubricating oil composition containing the reaction product of alkylphenol, formaldehyde and an alkylene polyamine such as diethylenetriamine, and lime. It showed the superior oxidation resistance over a sulfur-bridged phenate. U.S. Pat. No. 3,057,800 used monoethanolamine in place of diethylenetriamine.

U.S. Pat. No. 3,340,190 describes a lubricant composition containing a succinimide type dispersant and a calcium phenate prepared from nonylphenol, formaldehyde and ethylendiamine.

U.S. Pat. No. 3,368,972 describes a lubricating oil containing the calcium phenate from high molecular weight alkylphenol (molecular weight 600-3000), formaldehyde and polyalkyl polyamines. Instead of monophenols, sulfur-bridged phenols are also used.

U.S. Pat. No. 3,429,812 describes the overbasing of the third type of phenates.

From the foregoing, it can be seen that the prior art does not provide or make obvious an oil additive that will have the advantages of this invention including the reduced tendency to form lacquer and varnish deposits in the engine in which the lubricants containing the additives are employed and that has the superior antioxidant use of this invention.

SUMMARY OF THE INVENTION

Accordingly, it is an object of this invention to provide an oil additive that has the hereinbefore delineated advantages, including superior oxidation resistance and which is not obvious in view of the prior art.

Specifically, it is an object of this invention to provide an oil additive having reduced lacquer forming tendency, providing superior oxidation resistance to the oil as well as providing detergency and antiwear characteristics and basicity recognized as important in lubricants.

These and other objects will become apparent from the descriptive matter hereinafter.

In accordance with this invention, there is provided an additive for lubricating oils having a superior antioxidant performance with reduced tendency to form varnish and lacquer characterized by the alkaline earth metal salts of the reaction products formed by treating an alkylphenol and formaldehyde with a sulfur-containing polyalkylene amine, the products of which contain primarily a compound having the following generic formula:

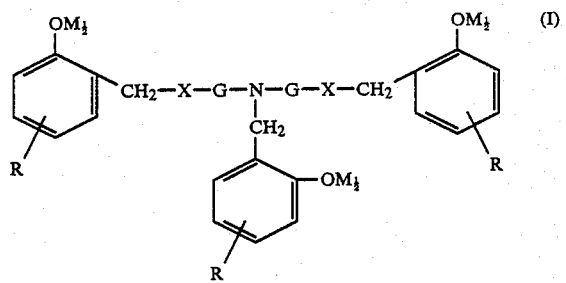

where:
X is selected from the group consisting of sulfur moiety and tertiary amine moiety;
G is an alkylene group containing 1 to 8 carbon atoms; and
R is an alkyl group containing 7 to 24 carbon atoms, and
M is an alkaline earth metal.

It is theorized that the compound represented by structural formula (I) is the compound responsible for the improved performance. There is improved performance by these reaction products formed by treating an alkylphenol and formaldehyde with a sulfur containing polyalkylene amine regardless of whether other by products are necessary for this or not and this invention is not to be limited to the consequences of any theory that the above compound represents. The reason for the improved performance of the lubricating oil having the additive in it is not totally clear but is believed to be due to the improved compound represented by structural formula (I).

BRIEF DESCRIPTION OF PREFERRED EMBODIMENTS

As indicated hereinbefore, the Mannich base type alkaline earth phenates are most effective in providing the improved oxidation and corrosion resistance demonstrated by the railroad diesel engine oils having the oil additive in it. This has been supported by many bench oxidation tests such as the Oxygen Absorption Test, the Sinclair Railroad Oxidation Test, the ARCO Railroad Oxidation Test and engine tests such as EMD 2-567 Engine Test. Oils containing this type of phenates invariably show lower uptake of oxygen, lower increases of acid number, viscosity and insolubles, lower loss of metals by corrosion, slower consumption of reserve basicity than oils containing other types of phenates. This superior oxidation resistance has been substantiated by actual performance in railroad diesel engines in prolonging drain periods, in saving the costs of oil and maintenance, and in prolonging the life of engines.

The superior performance is believed to have resulted at least in part, from the antioxidant and metal-deactivating capability of this type of phenates. They contain, in their molecules a number of atoms which can donate pairs of electrons to metals such as iron, copper and lead and form a chelate compound or complex; and, in so doing, they effectively eliminate or reduce the catalytic effects of these metals on oil oxidation.

One drawback of this type of additive is the stronger lacquer forming tendency of compounds containing the amine groups. Upon oxidation, nitro- and nitroso-compounds and sometimes nitrates are formed. These compounds can be converted to lacquer or varnish under severe engine conditions. The lacquer and varnishes can also serve as binders for carbonaceous deposits. The result is increases in both lacquer and carbon deposits on engine parts. For diesel engines these compounds can increase piston ring groove and land deposits and then cause ring sticking and engine failure. The problem becomes increasingly more severe as new engine designs raise temperatures and pressures of the piston ring belt area and reduce oil flow thereto.

The invention described hereinbefore is accomplished by replacing the polyalkylene polyamines used in preparing the normal Mannich-base type phenates with sulfur-containing polyalkylene amines. One example of these compounds is di(2-mercaptoethyl) amine, $(HSCH_2CH_2)_2NH$. When three moles of tertiary octylphenol, three moles of formaldehyde, and one mole of di(2-mercaptoethyl) amine are reacted in a solvent or carrier oil and then treated with lime, or calcium hydroxide, the following compound (II) is formed among the reaction products and is believed to contribute significantly to the efficacy of this oil additive.

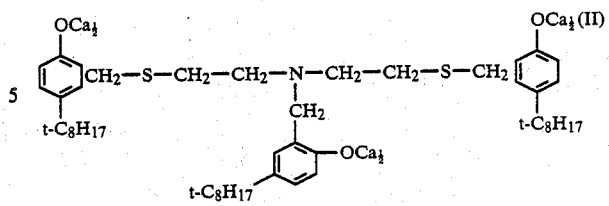

This compound contains only one-third of the nitrogen content of a similar compound prepared from the same reactants except that diethylene triamine is used instead of di(2-mercaptoethyl) amine. This can be seen clearly from the following equation resulting in compound (III).

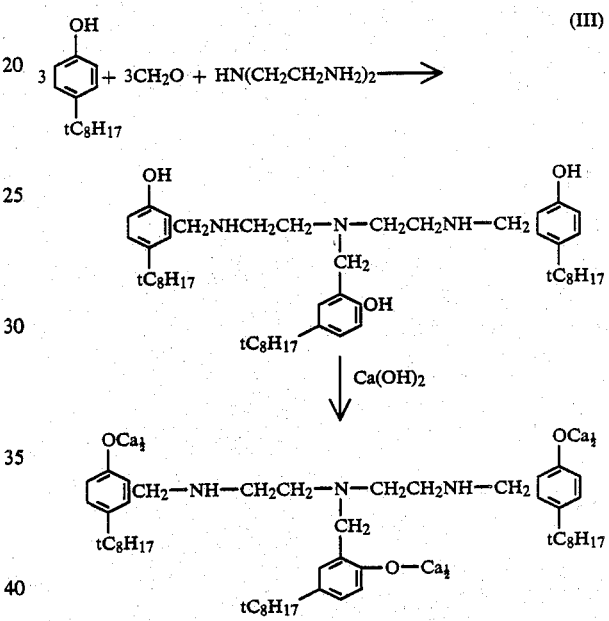

As can be seen there are three amine groups in (III) and only one tertiary amine group in (II). By eliminating two out of three amine groups, which can be oxidized to nitro-, nitroso-, and nitrate compounds, the lacquer-forming tendency and amount of lacquer and carbon deposits on engine parts can be substantially reduced. On the other hand, since the sulfur atoms in (II) can donate pairs of electrons to catalytic metals and form chelates, their effectiveness as metal deactivators is retained. Their effectiveness as anti-oxidants should be improved, since the phenate groups remain the same and the two —S— groups should provide additional anti-oxidant capability.

Compounds suitable for the replacement of diethylenetriamine and other polyalkylene polyamines include secondary amines of the following formula: $(HSG)_2NH$ wherein:

G equals $-CH_2CH_2-$, $-CH_2-CH-CH_3$, $-CH_2CH_2CH_2-$ or a $C_4-C_8$ alkylene group and 2 G's can be the same or different.

Also in another embodiment of this invention, the two primary amine groups in diethylene triamine are replaced with secondary amine groups, $(YNHCH_2CH_2)_2NH$, where:

Y is methyl, ethyl, isopropyl, n-propyl or a $C_4$ to $C_8$ alkyl group.

by this approach, the secondary amine groups which are believed to be more susceptible to lacquer and varnish formation are replaced with tertiary amine groups to yield phenates represented by formula (IV):

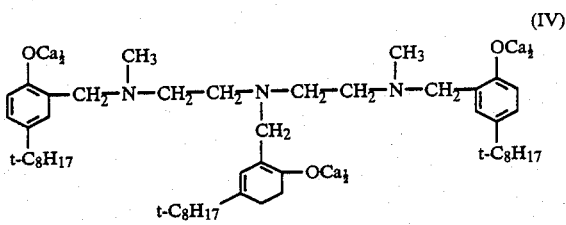
(IV)

The following examples illustrate how the improved lubricating oil additives can be prepared and used to provide lubricating oils having superior oxidation and corrosion resistance, as well as good anti-wear characteristics and engine cleanliness and durability.

EXAMPLE I

A 5-liter, 3-necked flask is equipped with a heating mantle, a mechanical stirrer, a dropping funnel and a water separating trap. 1236 grams (6 moles) of p-tert-octylphenol is placed in the flask and heated to 85° C. In the dropping funnel is placed 274 grams (2 moles) of di(2-mercaptoethyl) amine. With mechanical stirring the amine is added dropwise over a period of thirty minutes. In the dropping funnel is then placed 487 grams (6 moles, 37%) of formalin, which is added slowly into the flask over a period of two hours in which the temperature of the reaction mixture is raised to 160° C. Water is removed periodically from the trap. The mixture is heated at 160° C. until no more water distils into the trap. Upon cooling to about 100° C., 2,000 grams of a paraffinic base oil having a viscosity of about 150 SUS at 100° F. and a viscosity index of 95 is added. This is followed with 4 moles of hydrated lime and 200 ml of water. The mixture is then heated at 150° C. with stirring for a period of three hours or until the water removal is completed. To the reaction mixture is added 1% of Hyflo Super-Cel and the mixture is filtered through a Buchrer funnel using a vacuum. The product is a mineral oil solution of a mixture containing the calcium phenate having the structural formula (II), believed to be the effective ingredient in the superior performance of this engine oil additive in accordance with this invention.

EXAMPLE II

The same preparation as in Example I is carried out except that the di(2-mercaptoethyl) amine is replaced by N,N'-dimethyl diethylene-triamine and the amount of each reactant is reduced by half. The reaction can be completed in a shorter period of time. The product is a mineral oil solution of a reaction product that includes the calcium phenate having structural formula (IV), believed to be responsible for superior performance of one embodiment of this invention.

The calcium phenates as illustrated in the above examples contain mineral oils and can be used directly in engine oil formulations. The concentrations to be used is dependent upon severity requirements of the engine oil and can vary from about 1% by weight to as much as 5% by weight on an active ingredients basis. The base oil to be used includes both paraffinic and naphthenic oils and is dependent upon the service required. For railroad diesel engine oils a mixture of paraffinic and napthenic oils is often required and a range of viscosity is specified by the engine builder. The phenates of this invention can also be advantageously used in synthetic and highly hydrogenated base oils. In diesel engine and other severe services, it is also advantageous to have the presence of other additives, including other calcium phenates (sulfur-or $CH_2$-bridged), calcium phenates which have been overbased by passing carbon dioxide in the presence of lime and promoter, other alkaline earth metals (magnesium, barium and the like) phenates, neutral and overbased alkaline earth metal sulfonates, ashless dispersants (succinimide or Mannich base type), or other anti-wear additives and friction modifiers.

Having thus described the invention, it will be understood that such description has been given by way of illustration example and not by way of limitation, reference to the latter purpose being had to the appended claims.

What is claimed is:

1. An antioxidant additive for lubricating oil having reduced tendencies to form lacquer comprising alkaline earth metal salts of the reaction products formed by treating an alkylphenol and formaldehyde with a sulfur-containing polyalkylene amine, which products contain

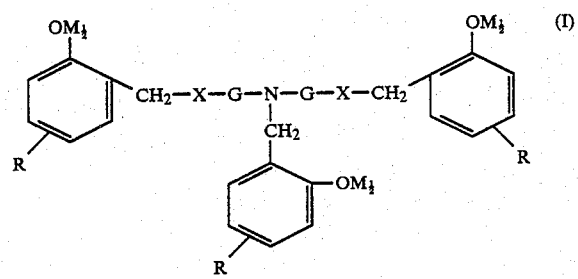
(I)

where:
X is selected from the group consisting of sulfur moiety, and a tertiary amine moiety;
G is an alkylene group containing 1 to 8 carbon atoms;
R is an alkyl group containing 7 to 24 carbon atoms; and
M is an alkaline earth metal.

2. The antioxidant oil additive of claim 1 wherein the reaction products contain a compound having the structural formula as follows:

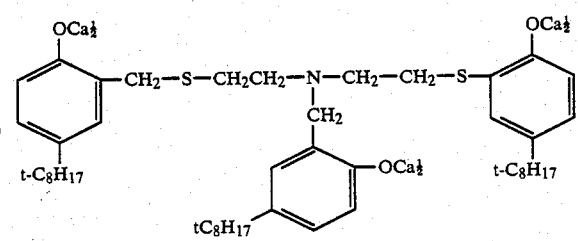

3. The antioxidant additive of claim 1 wherein the reaction products contain the compound having the following structural formula:

7
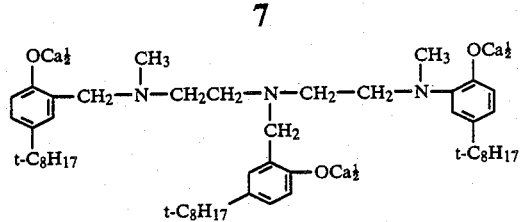
* * * * *
8
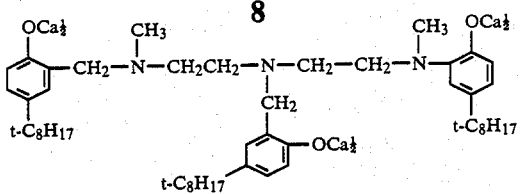
* * * * *

UNITED STATES PATENT OFFICE
CERTIFICATE OF CORRECTION

PATENT NO. : 4,861,504
DATED : August 29, 1989
INVENTOR(S) : Tai S. Chao

It is certified that error appears in the above-identified patent and that said Letters Patent is hereby corrected as shown below:

The formula appearing in Column 8 is deleted

Signed and Sealed this

Sixteenth Day of October, 1990

Attest:

HARRY F. MANBECK, JR.

*Attesting Officer*  *Commissioner of Patents and Trademarks*